(12) United States Patent
Kloster

(10) Patent No.: US 8,839,816 B2
(45) Date of Patent: Sep. 23, 2014

(54) SINGLE OPERATION CONTROL MECHANISM FOR A PRESSURIZED GAS ORAL CLEANING APPLIANCE

(75) Inventor: Tyler G. Kloster, Snoqualmie, WA (US)

(73) Assignee: Koninklijke Philips N.V., Eindhoven (NL)

( * ) Notice: Subject to any disclaimer, the term of this patent is extended or adjusted under 35 U.S.C. 154(b) by 299 days.

(21) Appl. No.: 13/381,765

(22) PCT Filed: Jun. 16, 2010

(86) PCT No.: PCT/IB2010/052707
§ 371 (c)(1),
(2), (4) Date: Dec. 30, 2011

(87) PCT Pub. No.: WO2011/007272
PCT Pub. Date: Jan. 20, 2011

(65) Prior Publication Data
US 2012/0102672 A1    May 3, 2012

Related U.S. Application Data

(60) Provisional application No. 61/225,936, filed on Jul. 16, 2009.

(51) Int. Cl.
*A61C 17/02* (2006.01)
*A61C 17/028* (2006.01)

(52) U.S. Cl.
CPC .............. *A61C 17/02* (2013.01); *A61C 17/028* (2013.01)
USPC ............................................. 137/613; 433/216

(58) Field of Classification Search
USPC ........................................ 137/613; 433/216
See application file for complete search history.

(56) References Cited

U.S. PATENT DOCUMENTS

| 4,802,508 A | * | 2/1989 | Styles et al. ............ 137/624.13 |
| 5,208,933 A | * | 5/1993 | Lustig et al. .................. 15/22.1 |
| 5,628,490 A | | 5/1997 | Roberts et al. |
| 5,697,784 A | | 12/1997 | Hafele et al. |
| 6,247,929 B1 | | 6/2001 | Bachman et al. |

FOREIGN PATENT DOCUMENTS

| EP | 0515118 A1 | 11/1992 |
| WO | 2008012707 A2 | 1/2008 |
| WO | 2009077923 A1 | 6/2009 |

\* cited by examiner

*Primary Examiner* — Kevin Lee

(57) ABSTRACT

The control mechanism (18) for a pressurized-gas oral cleaning appliance (10) includes a hollow valve member (44) for receiving gas from a pressurized source thereof (14) and for delivering gas to a gas exit assembly. A gas releasing assembly includes a user-activated actuation member (26) and a pusher member (36), wherein movement of the actuation member moves the pusher member and the valve member in a forward direction to a first position where gas enters the hollow interior of the valve. Further forward movement of the actuation member results in the valve member aligning with the pusher member in such a relationship that the valve member moves rearwardly by action of a spring (67) to a second position where the gas in the valve member exits through the openings and the groove to a gas exit line (68).

10 Claims, 4 Drawing Sheets

US 8,839,816 B2

SINGLE OPERATION CONTROL MECHANISM FOR A PRESSURIZED GAS ORAL CLEANING APPLIANCE

BACKGROUND OF THE INVENTION

This invention relates generally to oral cleaning appliances using fluid droplets and pressurized gas to accomplish cleaning of teeth, and more specifically concerns an actuating mechanism for release of bursts of pressurized gas within the appliance.

One type of oral cleaning appliance, particularly adapted for interdental cleaning, uses bursts of pressurized gas acting on a stream of liquid to produce liquid droplets, to accomplish the desired cleaning. The bursts of gas can be either air or $CO_2$. One example of such an appliance produces successive bursts of pressurized gas by operation of a user-operated control member such as a pushbutton or similar member. In such a system, it is important that, in operation of the control member, a single action in one direction acts to both charge a gas valve in the appliance with pressurized gas and then to subsequently discharge the gas from the valve in successive bursts to a nozzle assembly in which the droplets are produced and then delivered through an exit tip to the teeth for cleaning. The present invention accomplishes these desired objectives in a reliable and efficient manner.

Accordingly, the invention disclosed herein is a mechanism for controlling release of bursts of pressurized gas from a supply thereof for use in an oral cleaning apparatus, comprising: a hollow interior valve member having a rear end portion, the valve member having a valve wall with a circumferential groove therein, and a plurality of openings connecting the groove with the hollow interior of the valve member; an entrance line for gas extending from a supply thereof to an exterior surface of the valve member; an exit line for gas, extending from the exterior surface of the valve member to an exit assembly, wherein the gas exit line is offset longitudinally from the gas entrance line along the length of the valve member; and a releasing assembly, which includes a contact member operating against the rear end portion of the valve member, moving it forwardly from an initial nominal position to a position where the gas entrance line is aligned with the circumferential groove, permitting gas to enter, wherein the releasing assembly further includes a forward portion which is configured such that further forward movement of the releasing member results in the valve member moving rearwardly, aligning the valve member with the gas exit line, permitting gas to exit from the valve member to the gas exit assembly.

DETAILED DESCRIPTION OF THE PREFERRED EMBODIMENT

Figure 1:
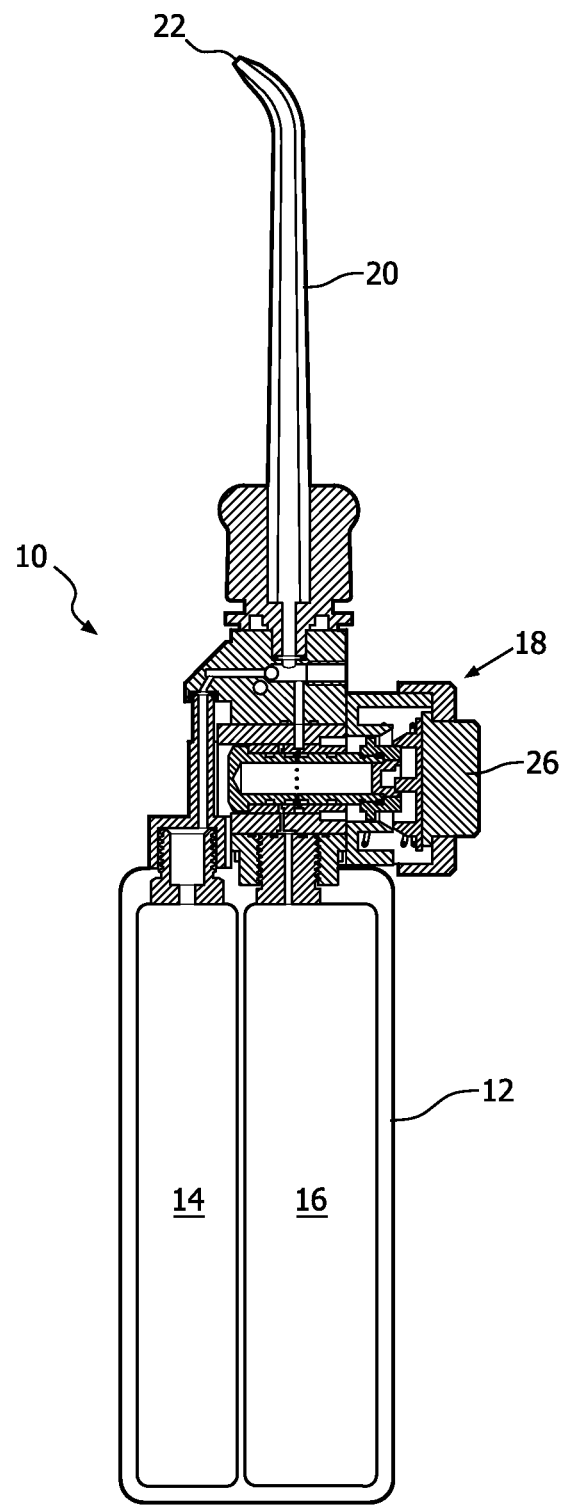
FIG. 1 is a cross-sectional view of a complete pressurized gas dental cleaning apparatus with the control mechanism disclosed herein.

FIG. 1 shows a complete interdental cleaning appliance 10 using successive bursts of pressurized gas to produce liquid droplets for dental cleaning. It includes a body portion 12 which in turn includes both a pressurized gas reservoir 14 and a fluid reservoir 16 which can hold water or other liquid. The appliance 10 also includes a single operation control mechanism, generally at 18, and a nozzle assembly 20 which includes an exit tip 22 from which a spray of fluid droplets is directed to the dental region.

In operation, pressurized gas is released in successive bursts by a user operating control mechanism 18. The pressurized gas intersects fluid from the fluid reservoir to produce a stream of liquid droplets and then accelerates them through nozzle assembly 20 and out exit tip 22. The fluid droplets are directed toward the teeth of the user, particularly the interdental regions, to clean plaque therefrom.

Figure 2:
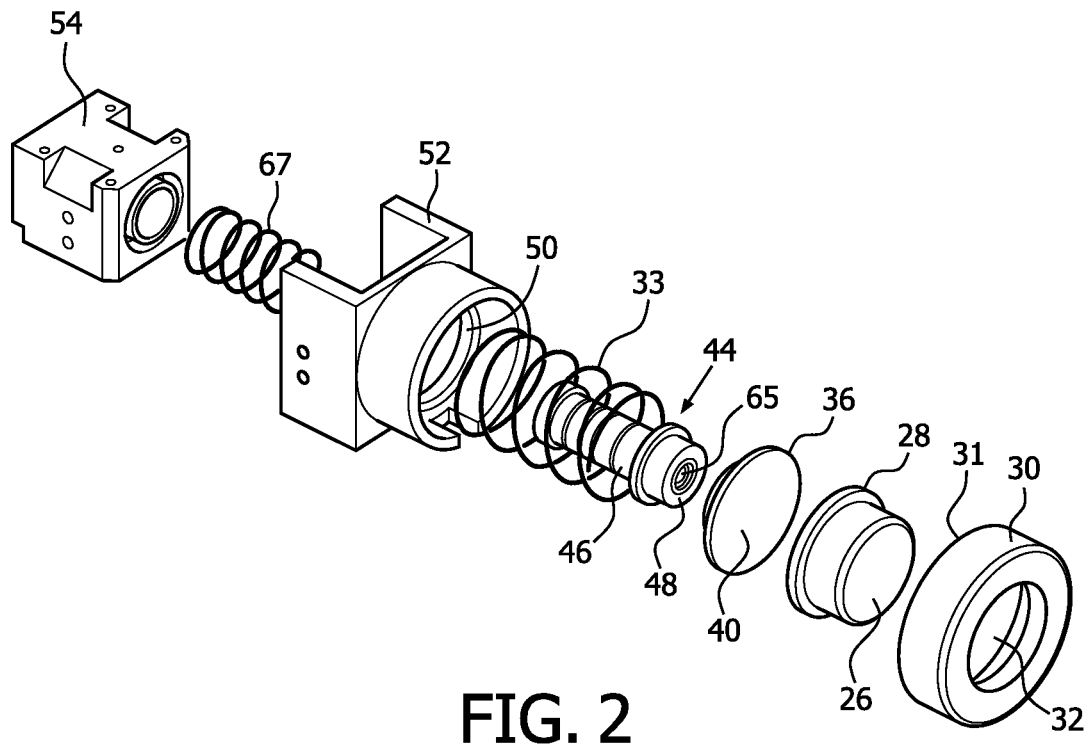
FIG. 2 is an exploded view of the control mechanism of FIG. 1.
Figure 3:
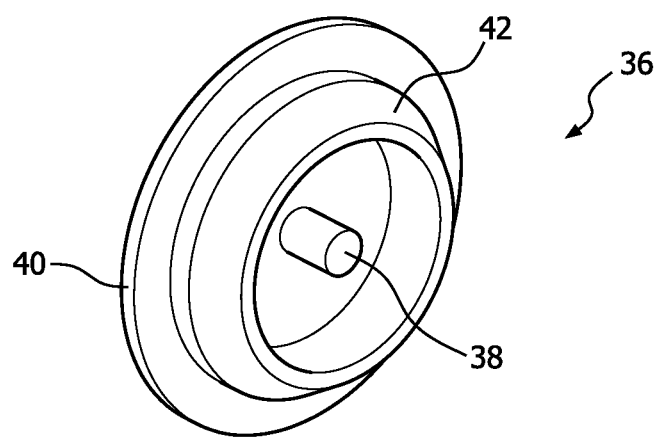
FIG. 3 is a perspective view of one element of the assembly of FIG. 2.
Figure 4:
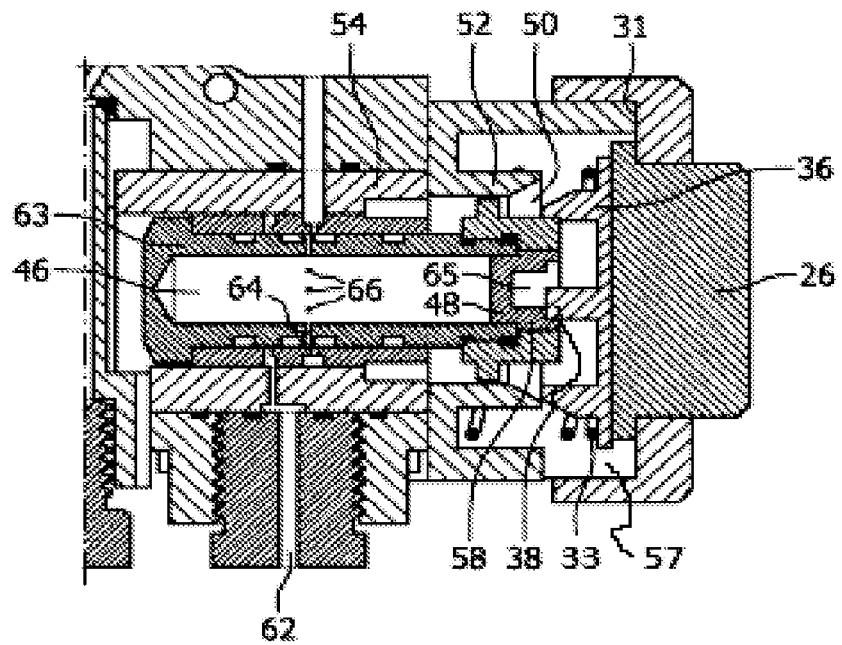
FIG. 4 is cross-sectional view of the control mechanism showing a first stage in the operation thereof.
Figure 5:
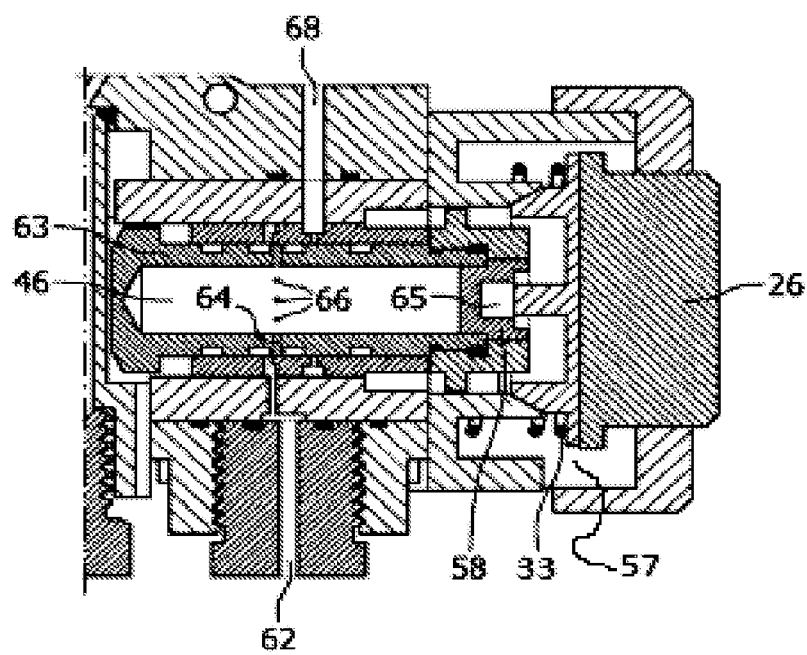
FIG. 5 is a cross-sectional view showing a second stage in the operation of the control mechanism.
Figure 6:
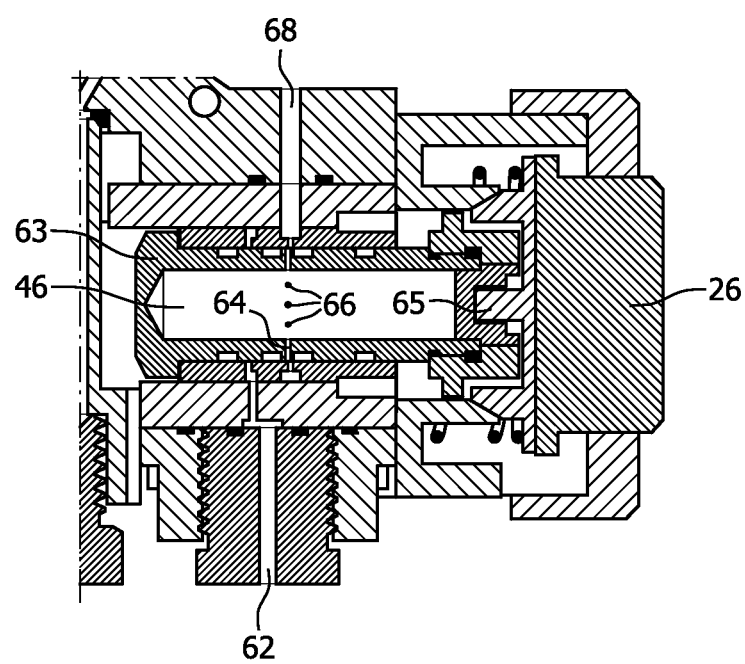
FIG. 6 is a cross-sectional view showing a third stage in the operation of the control mechanism.

Control mechanism 18 is shown in more detail in exploded form in FIGS. 2 and 3, and in successive stages of operation in FIGS. 4-6. Control mechanism 18 includes a cylindrical pushbutton member 26 for operation by the user. The pushbutton 26 can take various forms and configurations in addition to a pushbutton. In the embodiment shown, pushbutton 26 is cylindrical with a small lip 28 extending outwardly from the remainder of the push button at a forward end 29 thereof. The pushbutton 26 moves back and forth in an annular shoulder member 30, which acts as a guide for movement of the pushbutton. Shoulder member 30 includes a central opening 32 through which the body of the pushbutton member extends. The extending lip 28 tends to remain against the forward edge 31 of shoulder 30 by action of a pushbutton return spring 33. Forward movement of pushbutton 26 and pushbutton lip 28 is against spring 33.

Positioned adjacent the forward end 29 of pushbutton 26 is a push rod member 36 with a central rod member 38. The push rod member 36 includes a flat circular portion 40 having approximately the same diameter as the pushbutton member 26 and approximately 1-3 mm thick. The push rod member 36 includes an exterior chamfer portion 42 and a central rod member 38. In the embodiment shown, the rod member is approximately 1-4 mm in diameter, while the chamfer portion 42 has a chamfer angle in the range of 20°-70°, but preferably approximately 60°.

Rod member 38 of the push rod member 36 operates against a rear end 48 of a valve assembly 44, which has a hollow interior 46. Chamfer portion 42 of the push rod member 36 engages a mating surrounding chamfer portion 50 on a switch housing member 52. Chamfer portion 42 on push rod member 36 mates with chamfer portion 50 on the switch housing to produce an aligning action between valve assembly 44 and push rod assembly 36, as described in more detail below.

Forward of the switch housing 52 is a valve housing 54 into which the valve assembly 44 fits and moves back and forth in operation.

FIG. 4 shows the start position of the control mechanism, involving the entry of gas into and exit from the valve assembly. In the start position, pushbutton 26 is in its rearmost position with lip 28 adjacent forward edge 31 of shoulder 30. In this position, the assembly valve 44 is in its rearmost position in the valve housing and is completely closed, to either entry of gas or exit of gas therefrom. In this position, rod member 38 is against a shoulder portion 58 of a rear end 48 of the valve assembly. In one embodiment, the shoulder portion has a step configuration. The push rod member 38 is in this off-center position by the action of a magnet 57. As pushbutton 26 is moved forwardly, with rod member 38 pushing on shoulder portion 58 of valve assembly 44, the valve assembly is moved forwardly within valve housing 54, until entry line 62 from gas reservoir 14 lines up with a continuous circular groove or trough 64 in the wall 63 of valve assembly 44, around the circumference of valve assembly 44. The groove 64 is similar to a circumferential line, but with depth, approximately 8-12 mm in diameter. Connecting the circular groove 64 to the interior 46 of the valve assembly is a series of openings 66-66 at spaced points around the periphery of the valve assembly. Typically, there are 6-8 spaced openings, equally spaced, although this number and the spacing can vary.

Pressurized gas enters the circular groove 64 when pushbutton 26 is momentarily in the position shown in FIG. 5. As valve assembly 44 is moved forwardly by the action of the user moving pushbutton 26, gas entry line 62 will come into momentary fluid communication with circular groove 64. The gas in the circular groove will move through openings 66 into the interior 46 of the valve, filling it with a selected amount of pressurized gas.

As the valve assembly 44 is moved slightly further forward by the user continuing to push on pushbutton 26, chamfer surface 42 of push rod member 36 engages chamfer surface 50 of switch housing 52 in such a manner that push rod member 36 moves laterally across the forward end 28 of the pushbutton, until rod member 38 aligns with a center cavity 65 in the rear end 48 of the valve assembly. When rod member 38 is initially aligned with the cavity 65, a valve return spring 67, shown in FIG. 2, moves the valve assembly 44 quickly to the rear, while the pushbutton is still in a forward position, so that the rod member 38 fully engages cavity 65, as shown in FIG. 6.

During this movement, grove 64 in the valve assembly is moved out of alignment with entry line 64 and into alignment with gas exit line 68. This occurs while pushbutton 26 is still in its most forward position, as shown in FIG. 6. Rod member 38 is abutting the forward end of cavity 65. In this position of the valve assembly 44, the gas in the interior 46 of the valve assembly 44 moves through openings 66, into circular groove 64 and then into exit line 68, from where it moves into nozzle assembly 20, where it intercepts fluid from fluid reservoir 14, producing liquid droplets. The above action produces a single burst of gas and a resulting single burst of liquid droplets, which are accelerated out of the nozzle and the exit tip 22 to the teeth.

When pushbutton 26 is then released, magnet 57 draws the push rod member 36 laterally so that rod member 38 once again is positioned against shoulder portion 58 of the rear end of the valve assembly, out of alignment with cavity 65. Pushbutton 26 is returned to its initial position by spring 33. The control mechanism is thus once again in its start position (FIG. 4).

Hence, a control mechanism has been shown and described which results in a burst of gas from a pressurized gas reservoir entering a valve chamber and then exiting the valve chamber while the pushbutton is moved only in a forward direction. All of the action of the valve, specifically the entry of gas and the exit of gas in successive bursts is produced by forward motion only of the pushbutton. Spring 33 returns pushbutton 26 to its start position when pressure on the pushbutton is released, and a magnet moves the push rod member back into its starting position, ready for the next successive action by the user against the pushbutton to produce the next burst of gas.

Although a preferred embodiment of the invention has been disclosed for purposes of illustration, it should be understood that various changes, modifications and substitutions may be incorporated in the embodiment without departing from the invention which is defined by the claims which follow:

The invention claimed is:

1. A mechanism for controlling release of bursts of pressurized gas from a supply thereof for use in an oral cleaning apparatus (10), comprising:
    a hollow interior valve member (44) having a rear end portion (48), the valve member having a valve wall (63) with a circumferential groove (64) therein, and a plurality of openings (66) connecting the groove with the hollow interior (46) of the valve member;
    an entrance line (62) for gas extending from a supply thereof (14) to an exterior surface of the valve member;
    an exit line for gas (68), extending from the exterior surface of the valve member to an exit assembly, wherein the exit line for gas is offset longitudinally from the entrance line for gas along the length of the valve member; and
    a releasing assembly (18), which includes a contact member (38) operating against the rear end portion of the valve member, moving the valve member forwardly from an initial nominal position to a position where the gas entrance line is aligned with the circumferential groove, permitting gas to enter, wherein the releasing assembly includes a forward portion which is configured such that further forward movement of the releasing assembly results in the valve member moving rearwardly, aligning the valve member with the gas exit line, permitting gas to exit from the valve member to the gas exit assembly.

2. The mechanism of claim 1, including a first spring (33) to return the releasing member to its initial position and a second spring (67) to move the valve member rearwardly.

3. The mechanism of claim 1, wherein the releasing assembly includes an actuating member operated by a user and a pusher member (36) which includes the contact member at a forward end thereof, wherein the pusher member includes an outboard portion (42) which is chamfered inwardly, said chamfer mating with a correspondingly chamfered portion (50) of a housing member (52) surrounding the rear end portion of the valve member, the rear end portion including a shoulder (58) and a central cavity (65), wherein the pusher member is initially positioned such that the contact member contacts the shoulder of the rear end portion of the valve member, moving the valve member to the position where gas enters the valve member, and wherein interaction of the mating chamfered portions thereafter move the pusher member laterally, aligning the contact member with the central cavity, at which time a second spring moves the valve member rearwardly to the point where gas can exit from the valve member.

4. The mechanism of claim 1, wherein the openings are equally spaced around the circumference of the valve member, approximately 6-8 in number.

5. The mechanism of claim 3, including a magnet member (57) for maintaining the pusher member in a laterally offset position when the pusher member is in the initial position, such that the contact member abuts the shoulder of the rear end portion of the valve member.

6. The mechanism of claim 3, wherein the cavity in the rear end portion of the valve member is centered approximately on the hollow interior of the valve member.

7. The mechanism of claim 3, wherein the shoulder of the rear end portion of the valve member includes a step portion immediately surrounding the cavity, and wherein the contact member abuts the step portion when the mechanism is in its initial position and as the valve member is moved to a position where gas enters the valve member.

8. The mechanism of claim 3, wherein the actuating member is a pushbutton (26).

9. The mechanism of claim 3, wherein the mechanism is arranged such that gas enters the valve member and exits the valve member during the time that the actuating member is moving in a forward direction.

10. The mechanism of claim 3, wherein the pusher member is not physically connected to the actuating member, such that the pusher member is free to move laterally relative to the actuating member, and wherein the mechanism includes a magnet for acting on the pusher member to move the pusher member such that the contact member abuts the shoulder of the rear end portion of the valve member when the actuating member is in an initial nominal position.

* * * * *